(12) United States Patent
Clark

(10) Patent No.: US 9,700,323 B2
(45) Date of Patent: Jul. 11, 2017

(54) MEDICAL DEVICES HAVING FIXATION ANCHOR

(71) Applicant: Boston Scientific Scimed, Inc., Maple Grove, MN (US)

(72) Inventor: Christopher J. Clark, St. Michael, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 23 days.

(21) Appl. No.: 14/145,035

(22) Filed: Dec. 31, 2013

(65) Prior Publication Data
US 2014/0188157 A1    Jul. 3, 2014

Related U.S. Application Data

(60) Provisional application No. 61/747,572, filed on Dec. 31, 2012.

(51) Int. Cl.
*A61B 17/08* (2006.01)
*A61B 17/12* (2006.01)
(Continued)

(52) U.S. Cl.
CPC .. *A61B 17/12172* (2013.01); *A61B 17/12122* (2013.01); *A61F 2/01* (2013.01);
(Continued)

(58) Field of Classification Search
CPC .... A61F 2/013; A61F 2/01; A61F 2220/0016; A61F 2002/018; A61B 17/0057;
(Continued)

(56) References Cited

U.S. PATENT DOCUMENTS 6,231,561 B1 *   5/2001   Frazier et al. ............... 604/500
7,727,189 B2     6/2010   VanTassel et al.
(Continued)

FOREIGN PATENT DOCUMENTS

CN     1399571 A     2/2003
EP     1595504       11/2005
(Continued)

OTHER PUBLICATIONS

Notification of Transmittal of the International Search Report and the Written Opinion of the International Searching Authority, or the Declaration for Application No. PCT/US2013/078454, mailed on Apr. 22, 2014 (13 pgs.).
(Continued)

*Primary Examiner* — Richard Louis
(74) *Attorney, Agent, or Firm* — Seager, Tufte & Wickhem, LLP

(57) ABSTRACT

A medical device including a medical device body that includes a first support structure, the medical device further comprising a first fixation anchor that includes a first anchor body extending between a first end and an opposing second end, and a hook portion extending from the first end, wherein the first anchor body engages the first support structure, and wherein the first fixation anchor is fabricated separate and apart from the medical device body. A method of making a medical device is disclosed.

15 Claims, 4 Drawing Sheets

(51) Int. Cl.
*A61F 2/01* (2006.01)
*A61B 17/00* (2006.01)

(52) U.S. Cl.
CPC ........ *A61F 2/013* (2013.01); *A61B 17/12109* (2013.01); *A61B 2017/00477* (2013.01); *A61B 2017/00526* (2013.01); *A61B 2017/00579* (2013.01); *A61B 2017/00632* (2013.01); *A61F 2002/018* (2013.01); *A61F 2220/0016* (2013.01); *Y10T 29/49826* (2015.01)

(58) Field of Classification Search
CPC ........ A61B 17/12122; A61B 17/12172; A61B 17/12109; A61B 2017/00526; A61B 2017/00477; A61B 2017/00632
USPC .......................................... 606/200
See application file for complete search history.

(56) References Cited

U.S. PATENT DOCUMENTS

| | | | |
|---|---|---|---|
| 7,972,359 | B2 | 7/2011 | Kreidler |
| 8,221,384 | B2 | 7/2012 | Frazier et al. |
| 8,562,509 | B2 | 10/2013 | Bates |
| 2003/0208214 | A1* | 11/2003 | Loshakove et al. .......... 606/153 |
| 2004/0220682 | A1 | 11/2004 | Levine et al. |
| 2005/0125020 | A1 | 6/2005 | Meade |
| 2009/0005803 | A1 | 1/2009 | Batiste |
| 2011/0054515 | A1* | 3/2011 | Bridgeman ........ A61B 17/0057 606/200 |
| 2012/0172654 | A1 | 7/2012 | Bates |
| 2012/0245619 | A1* | 9/2012 | Guest ................ A61F 2/01 606/200 |
| 2014/0188157 | A1 | 7/2014 | Clark |

FOREIGN PATENT DOCUMENTS

| | | |
|---|---|---|
| EP | 2481381 | 8/2012 |
| JP | 2003532457 A | 11/2003 |
| JP | 2005324019 A | 11/2005 |
| JP | 2007513684 A | 5/2007 |
| WO | 00/35352 | 6/2000 |
| WO | 03/032818 | 4/2003 |
| WO | 2007/044536 | 4/2007 |
| WO | 2014106239 A1 | 7/2014 |

OTHER PUBLICATIONS

Cline, "File: Fish hooks.jpg," Wikipedia Foundation, Inc,. San Francisco, CA, Jun. 2007; p. 1 of 4; available online at http://en.wikipedia.org/wiki/File:Fish_hooks.jpg; last accessed Oct. 5, 2012.

* cited by examiner

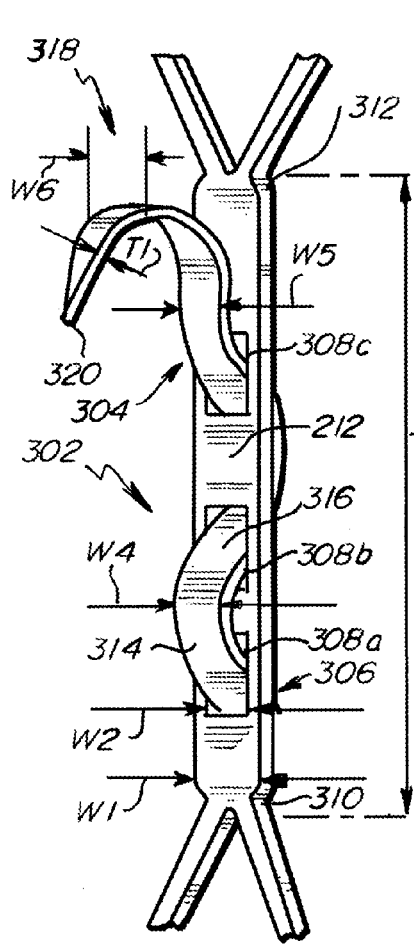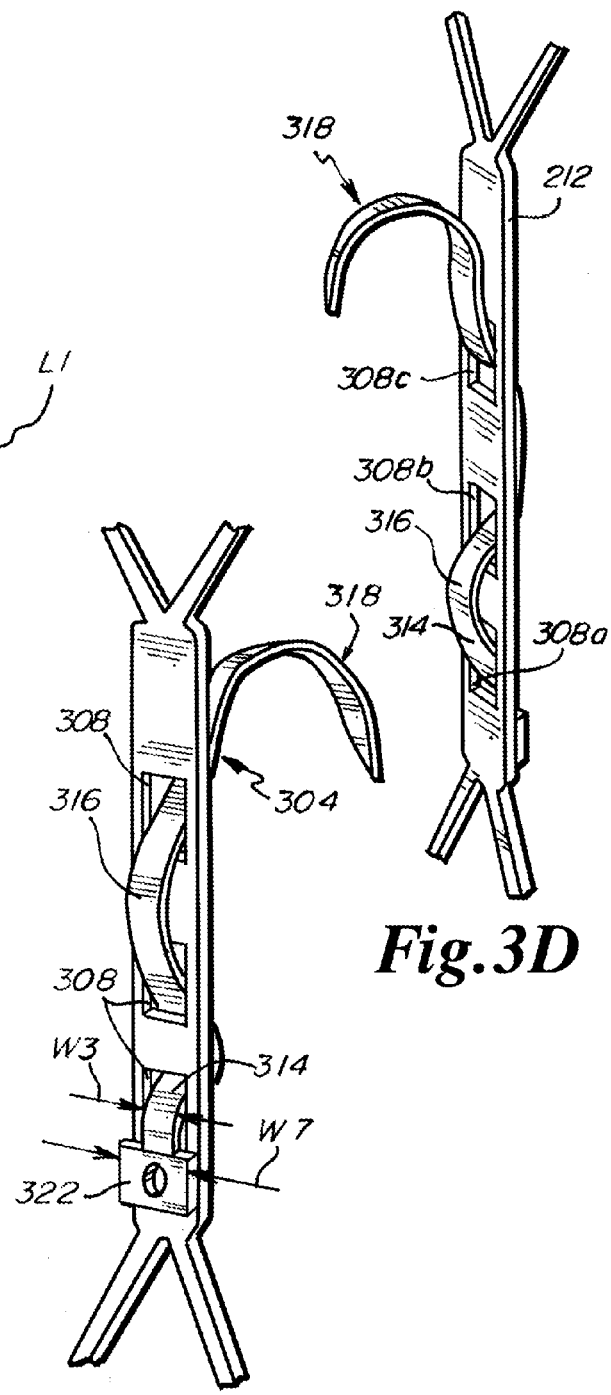
*Fig.3B*
*Fig.3C*
*Fig.3D*

MEDICAL DEVICES HAVING FIXATION ANCHOR

CROSS-REFERENCE TO RELATED APPLICATIONS

This application claims the benefit of U.S. Provisional Application Ser. No. 61/747,572, the contents of which is hereby incorporated by reference.

FIELD

This disclosure relates to a medical device that may be, for example, implanted into a portion of a heart. Particularly, it relates to a medical device for to be placed in the left atrial appendage (LAA) of the heart, wherein the medical device has features pertaining to fixation of the occlusion device to a target tissue and to other adjoining areas.

BACKGROUND

The left atrial appendage (LAA) is a small conical projection in the upper anterior portion of the left atrium of a heart. In certain heart conditions (e.g., abnormal heart conditions), there is a possibility of blood accumulating in the LAA, which may lead to formation of clots/emboli. The clots may migrate to the circulatory system and cause serious problems, such as a stroke.

There exist various medical devices to block emboli formed in the LAA from entering the circulatory system. These medical devices may need an anchor mechanism for fixation with the LAA so as to prevent migration (e.g., acute, chronic) of the devices from the LAA to other areas of the left atrium. The anchor mechanism may generally include fins or barbs that can hold onto tissues of the LAA. The anchor mechanism (e.g., fins or barbs) is fabricated as an integral part of the medical device.

This integration of the anchor mechanism into a medical device can increase the length of the medical device and reduce its radial strength. The process of fabricating the anchor mechanism, as an integral structure of the medical device, may complicate the manufacturing process and thereby increase cost of production. The integration of the anchor mechanism may result in anchor mechanism dimensions being influenced by the medical device requirements. In the case of the integral structure, various dimensions of the anchor mechanism are dependent on the medical device's parameters; for example, profile, wall thickness and the like. This may restrict the ability to increase or decrease the dimensions or strength of the anchor mechanism. Removal of the medical device with the integrated anchor mechanism from the body can also be difficult and may bear an increased risk of tissue damage.

Thus, there exists a need for improved medical devices that reduce or eliminate one or more deficiencies of previous medical devices.

Without limiting the scope of the present disclosure, a brief summary of some of the claimed embodiments of the present disclosure is provided below. Additional details of the summarized embodiments and/or additional embodiments of the present disclosure can be found in the detailed description.

A brief abstract of the technical disclosure in the specification is provided as well for the purposes of complying with 37 C.F.R. 1.72. The abstract is not intended to be used for interpreting the scope of the claims.

All US patents and applications, and all other published documents mentioned anywhere in this application are incorporated herein by reference, each in its entirety.

SUMMARY

In at least one embodiment, the present disclosure is directed to a medical device including a medical device body and a first fixation anchor. The medical device body can include a first support structure. The first fixation anchor can include a first anchor body extending between a first end and an opposing second end, and a hook portion extending from the first end. The first anchor body can engage (e.g., removably engage, temporarily engage, permanently engage, etc.) with the first support structure. The first fixation anchor can be fabricated separate and apart from the medical device body. The first fixation anchor can be formed from a first material and the medical device body is formed from a second material that is either same as or different from the first material.

In at least one embodiment, the present disclosure is directed to a method of making a medical device. The method can include providing a medical device body including a first support structure. The method can further include providing a first fixation anchor formed separate and apart from the medical device body. The method can further include attaching the first fixation anchor to the first support structure. The first fixation anchor can be structured and arranged to be detached from the first support structure and reattached to the first support structure or to a second support structure of the first medical device body or to a second medical device body.

BRIEF DESCRIPTION OF THE FIGURES

The present disclosure and the following detailed description of certain embodiments thereof can be understood with reference to the following figures:

FIG. 3B illustrates a perspective view of a support structure and a fixation anchor engaging with (e.g., coupled to) the support structure, in accordance with at least one embodiment of the present disclosure.

FIG. 3C illustrates another view of a support structure and a fixation anchor engaging with the support structure, in accordance with at least one embodiment of the present disclosure.

FIG. 3D illustrates another perspective view of a support structure and a fixation anchor engaging with the support structure, in accordance with at least one embodiment of the present disclosure.

DETAILED DESCRIPTION

Figure 1:
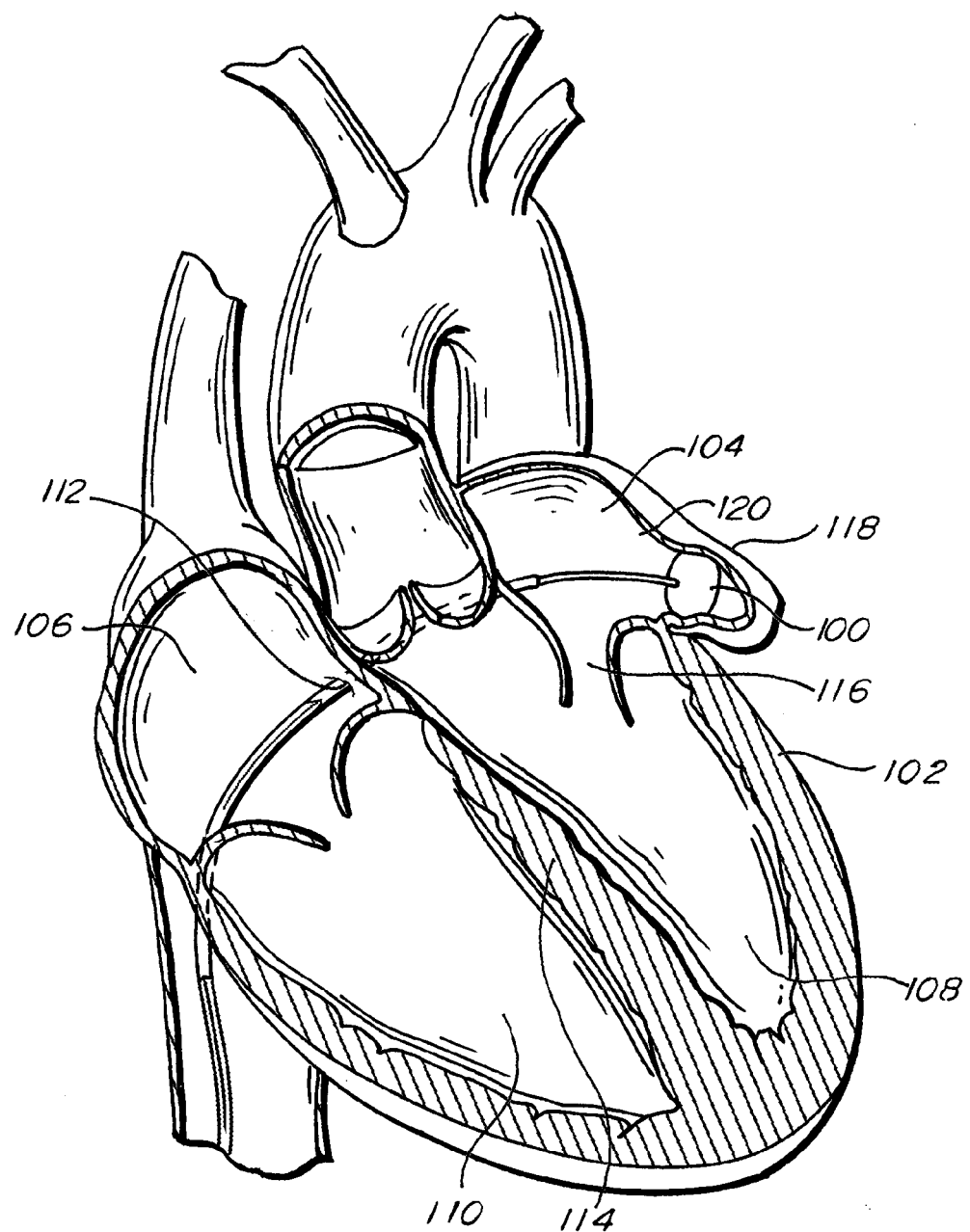
FIG. 1 illustrates a medical device operationally positioned in a heart of a patient, in accordance with at least one embodiment of the present disclosure.

While the subject matter of the present disclosure can be embodied in many different forms, specific embodiments of the present disclosure are described in detail herein. This description is an exemplification of the principles of the present disclosure and is not intended to limit the present disclosure to the particular embodiments illustrated.

For the purposes of this disclosure, like reference numerals in the figures, shall refer to like features unless otherwise indicated. For example, fixation anchors 302 in FIGS. 2, 3A-3F, and 4 have like reference numerals and share like features unless otherwise indicated. As another example, fixation anchors 302a and 302b (e.g., FIG. 3A) and fixation anchor 302 (e.g., FIGS. 2, 3A-3F, and 4) are considered to have like reference numerals herein and share like features unless otherwise indicated.

Various aspects of the present disclosure are depicted in the figures. Elements depicted in one figure can be combined with and/or substituted for elements depicted in another figure, as desired.

The terms "proximal" and "distal," described in relation to various devices, apparatuses, and components-as discussed herein-are referred with a point of reference. The point of reference, as used in this description, is a perspective of an operator. The operator can be a surgeon, a physician, a nurse, a doctor, a technician, and the like, who can perform a procedure of delivery and placement of the disclosed system/device into a patient's body as described herein. The term "proximal" refers to an area or portion that is relatively closer or closest to an operator (e.g., during a placement procedure). The term "distal" refers to an area or portion that is relatively farther or farthest from an operator (e.g., during a placement procedure).

Referring now to FIG. 1, illustrated is a medical device 100 placed inside a heart 102 of a patient, in accordance with at least one embodiment of the present disclosure. The heart has four chambers; two upper chambers called left atrium 104 and right atrium 106, and two lower chambers called left ventricle 108 and right ventricle 110. The two atriums 104 and 106 are separated from each other by a muscular wall, referred to as inter-atrial septum 112, and the ventricles 108 and 110 are separated from each other by a muscular wall, referred to as inter-ventricular septum 114. The left atrium 104 and the left ventricle 108 are separated by a mitral valve 116. The left atrium 104 has a small conical projection—called a left atrial appendage (LAA) 118—extending from an upper anterior portion 120 of the heart 102. As a part of physiology, the left atrium 104 receives oxygenated blood from lungs via a pulmonary vein. This blood is pumped by cardiac contraction in the left ventricle 108 via the mitral valve 116 for distribution throughout the circulatory system. In some cases, this may lead to an accumulation of pooling of blood in the left atrium 104 and the blood may get deposited in the LAA 118. As shown in FIG. 1, the medical device 100 of the present disclosure may be placed inside the LAA 118 to reduce (e.g., prevent) migration of blood clots formed in the LAA 118 to other parts of the circulatory system. In one or more embodiments, the medical device 100 can be an implantable medical device 100, an occlusion device, a left atrial appendage occlusion device, an interior vena cava filter, and/or the like.

In some embodiments, the medical device 100 can be placed using a catheter that can be advanced into the left atrium 104 through the inter-atrial septum 112 of a heart using a femoral approach. Other techniques for placement of a medical device of the present disclosure in, for example, the LAA may be apparent to one of skill in the art.

Figure 2:
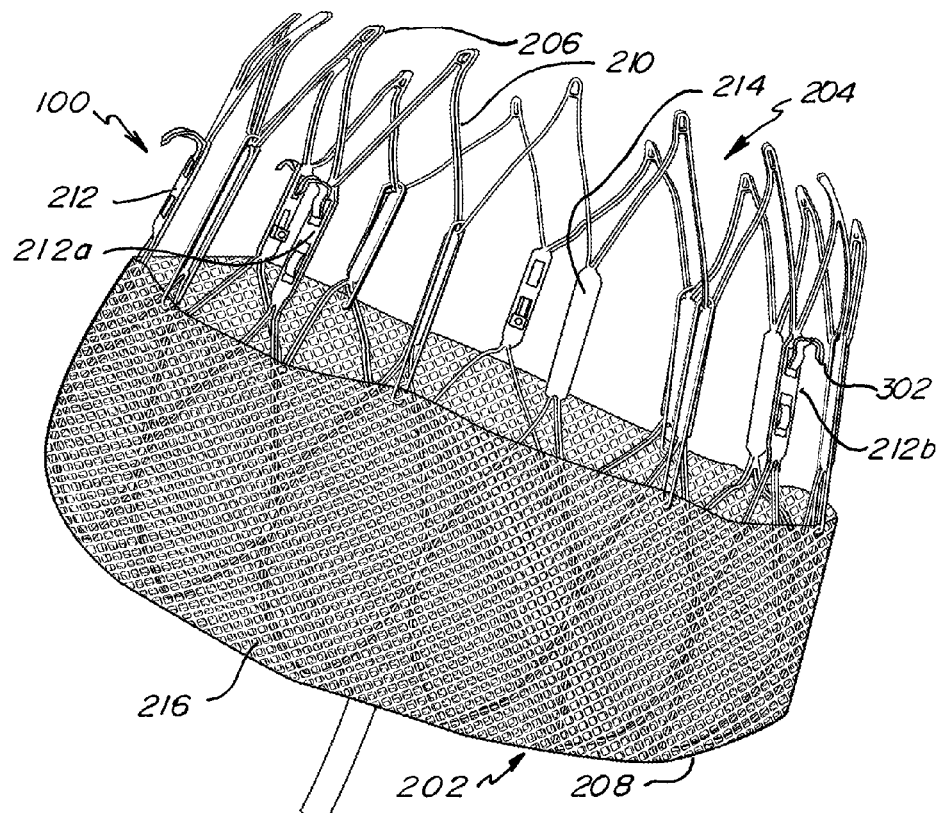
FIG. 2 illustrates an enlarged perspective view of a medical device having a medical device body, in accordance with at least one embodiment of the present disclosure.

FIG. 2 illustrates an enlarged perspective view of at least one embodiment of medical device 100. The medical device 100 has a proximal portion 202 and a distal portion 204. The medical device 100 includes a medical device body 206 and a covering 208. The medical device body 206 includes a frame 210 (e.g., a wire frame, a cage, etc.), and at least one support structure 212 (e.g., a first support structure 212a, a second support structure 212b, etc.). The frame 210 and the support structure 212 constitute a wall 214 extending from the proximal portion 202 to the distal portion 204. As also shown in FIG. 2, medical device 100 may include a fixation anchor 302, wherein at least a portion of the fixation anchor 302 engages at least a portion of the medical device body 206 (e.g., a support structure 212).

As shown in FIG. 2, a covering 208 (e.g., a basket) can be placed over at least a portion of the wall 214 toward the proximal portion 202 of the medical device 100 so as to peripherally surround at least a portion of the wall 214. For example, in at least one embodiment, the covering 208 can be configured to function as a cage filter for containing emboli in the LAA 118. For example, the covering 208 can act as a permeable filter, (e.g., to allow blood to pass through while preventing blood clots from exiting from the LAA 118 into the bloodstream). The covering 208 can include a plurality of pores 216. The pores 216 can have a pore size that may be variable. In some embodiments, the covering 208 can be formed from laser cut nitinol (e.g., nitinol wire). The covering 208 may be configured to facilitate closure of the LAA 118. In at least one embodiment, the covering 208 can be made up of biocompatible materials, such as, for example, expanded polytetrafluoroethylene (ePFTE) (e.g., Gortex®), polyester (e.g., Dacron®), (polytetrafluoroethylene) PTFE (e.g., Teflon®), silicone, urethane, metal fibers, or other biocompatible polymers, and combinations thereof. The covering 208 may include a wide variety of other suitable materials known to one of skill in the art.

Figure 3A:
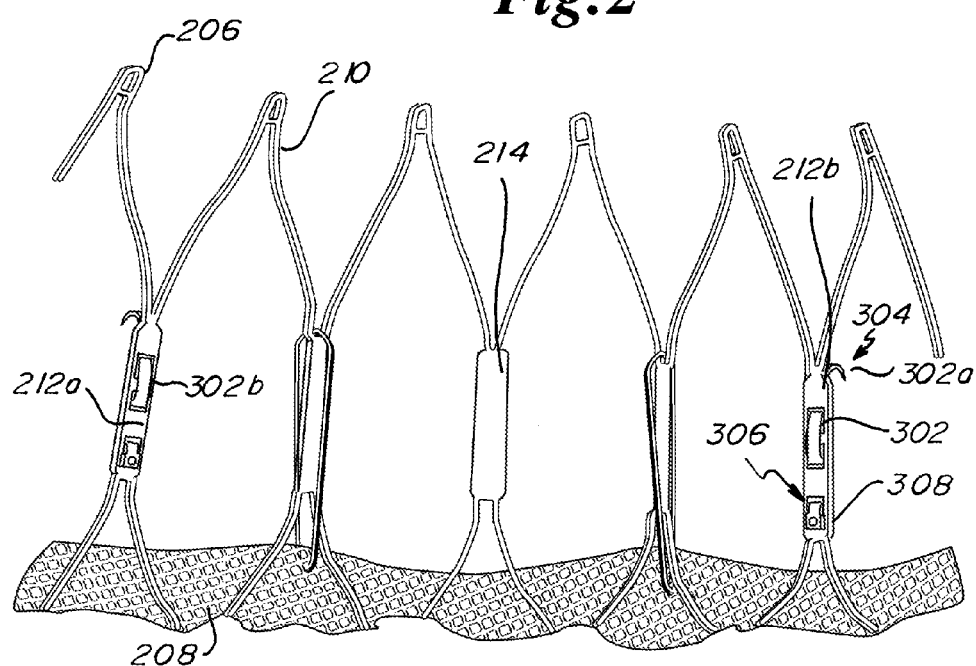
FIG. 3A illustrates a perspective view of a portion of a medical device body having two support structures and fixation anchor, in accordance with at least one embodiment of the present disclosure.

Referring now to FIG. 3A, a medical device 100 can include at least one fixation anchor 302, such as a first fixation anchor 302a and a second fixation anchor 302b. A fixation anchor, such as the fixation anchor 302a, defines a first end 304 and an opposing second end 306. The fixation anchor 302 includes a fixation anchor body 314 (see FIG. 3E) that extends between the first end 304 and the opposing second end 306 (e.g., from the first end 304 to the opposing second end 306). A fixation anchor 302 (e.g., first fixation anchor 302a, second fixation anchor 302b, etc.) can engage a support structure 212 (e.g., first support structure 212a, second support structure 212b, etc.). For example, as shown in FIG. 3A, the first fixation anchor 302a can engage the first support structure 212a and the second fixation anchor 302b can engage the second support structure 212b. A medical device of the present disclosure may include any suitable number (e.g., 1, 2, 3, 4, 5, 6, 7, 8, 9, 10, or more than 10) of fixation anchors. In at least one embodiment, a fixation anchor 302 can be constructed and arranged to be removably coupled to a support structure 212 (e.g., a first anchor body may be removable from a first support structure). In at least one embodiment, a fixation anchor 302 can be fabricated separate and apart from a support structure 212 of the medical device 100. In one or more embodiments, at least one fixation anchor is fabricated separate and apart from the medical device body and/or is removable from the medical device body. In at least one embodiment, all of the fixation anchors of a medical device are fabricated separate and apart from the medical device body and/or are removable from the medical device body. In at least one embodiment, a fixation anchor 302 can be formed from a first material and at least a portion of the medical device body 206, particularly the support structure 212, can be formed from a second material. In some embodiments, the first material can be same as the second material. In some embodiments, the first material can be different from the second material. Any of a wide variety of materials may be used to form one or more components of a medical device of the present disclosure (e.g., a fixation anchor, a medical device body, etc.).

The one or more embodiments disclosed herein may use the generic term "support structure 212" instead of the more specific terms "first support structure 212a" and the "second support structure 212b." The one or more embodiments disclosed herein may use the generic term "fixation anchor 302" instead of the more specific terms "first fixation anchor 302a" and the "second fixation anchor 302b." Also, it should be recognized that, in at least one embodiment, any fixation anchor 302 (e.g., first fixation anchor 302a, etc.) may be interchangeable between the first support structure 212a and the second support structure 212b or any other support structure 212. For example, a first fixation anchor 302a may be disengaged from (e.g., removed from) a first support structure 212a in order to engage first fixation anchor 302a with second support structure 212b. Also, in at least one embodiment, a second fixation anchor 302b can be interchangeable with the first fixation anchor 302a. For example, a first fixation anchor 302a may be disengaged from (e.g., removed from) a support structure 212 (e.g., first support structure 212a, etc.) and replaced by engaging a second fixation anchor 302b with the support structure previously engaged with first fixation anchor 302a. Although interchangeable fixation anchors may be identical in at least one embodiment, it may be recognized that interchangeability between fixation anchors does not necessarily mean that the fixation anchors are identical. As used herein, fixation anchors are considered to be interchangeable when a fixation anchor may be removed from a support structure of a medical device body and a second fixation anchor may engage the same or different support structure of the medical device body.

Referring now to FIGS. 3B-3C, a fixation anchor 302 is coupled (e.g., removably coupled) to a support structure 212, in accordance with at least one embodiment of the present disclosure. In FIG. 3B, the outward-facing surface of a support structure 212 is depicted. FIG. 3C illustrates another view of the support structure 212 and the fixation anchor 302 coupled to the support structure 212, in accordance with at least one embodiment of the present disclosure. In FIG. 3C, the inward-facing surface of support structure 212 is depicted.

In at least one embodiment, the support structure 212 can define at least one aperture 308 (e.g., a recess, a depression, an orifice, etc.) extending at least partially through the wall 214 of the medical device body 206. In at least one embodiment, the aperture 308 may extend through the support structure 212 to form an orifice. In some embodiments, the first support structure 212 can define more than one aperture 308 extending through the wall 214 of the medical device body 206, for example, a first aperture 308a, a second aperture 308b, and a third aperture 308c. The support structure 212 includes a proximal portion 310 and a distal portion 312, such that the proximal portion 310 is proximate the second end 306 of the fixation anchor 302 and the distal portion 312 can be proximate the first end 304 of the fixation anchor 302. The first support structure 212 defines a width W1 and a length L1 extending from the proximal portion 310 to the distal portion 312. In some embodiments, the width W1 can vary from the proximal portion 310 to the distal portion 312. In at least one embodiment, the support structure 212 can define one or more apertures 308 between the proximal portion 310 and the distal portion 312. In at least one embodiment, the support structure 212 may define more than one aperture 308. The aperture 308 may define a width W2 that may be shorter than the width W1 of the support structure 212. The one or more apertures 308 may be configured so as to receive at least a portion of the fixation anchor 302 there-through and/or therein.

With reference to FIG. 3B, the fixation anchor 302 includes an anchor body 314 extending from the first end 304 to the opposing second end 306 (see FIGS. 3C and 3E), and a central portion 316 defined between the first end 304 and the second end 306. The anchor body 314 defines a length L2 (see FIG. 3E) extending from the first end 304 to the second end 306. The second end 306 defines a width W3 (see FIG. 3C), the central portion 316 defines a width W4 (see FIG. 3B), and the first end 304 defines a width W5 (see FIG. 3B). In some embodiments, the widths W3, W4, and W5 can be uniform. Further, in at least one embodiment, as shown in FIGS. 3B and 3C, each of the widths W3, W4, and W5 is less than or equal to the width W2 of the aperture 308, which can be adapted to receive at least a portion of the anchor body 314.

In one or more embodiments of the present disclosure, the fixation anchor 302 can further include a hook portion 318 extending from the anchor body 314 (e.g., from the first end 304 of the anchor body 314). In some embodiments, the hook portion 318 may include a tissue engagement tip 320. In at least one embodiment, the hook portion 318 may terminate at the tissue engagement tip 320. The central portion 316 of the anchor body 314 can be disposed within a portion of the aperture 308.

In at least one embodiment, the hook portion 318 can be configured to extend from the first end 304 of the fixation anchor 302. The hook portion 318 defines a thickness T1, which, among other things, can influence one or more physical properties (e.g., strength, stiffness, resilience, etc.) of the hook portion 318. For example, for a given material, an increased thickness T1 may provide an increased stiffness (e.g., resistance to deformation in response to an applied force). In one or more embodiments, the hook portion 318 can include a tissue engagement tip 320 that is distal of the first end 304 of the fixation anchor 302. The hook portion 318 may include a width W6 that, in one or more embodiments, may decrease near the tissue engagement tip 320 relative to width W5 of the first end 304. In some embodiments, the tissue engagement tip 320 can have a configuration (e.g., sharp, pointed, etc.) to, for example, engage (e.g., tether) the tissues of the LAA 118, thereby facilitating fixation of the medical device 100 with the LAA 118. In the present disclosure, the hook portion 318 may take any of a wide variety of shapes or configurations known to one of skill in the art that may be suitable to, for example, engage tissues of the LAA 118. For example, the hook portion 318 can define a curved (e.g., J-shaped, C-shaped, U-shaped, circular arc-shaped, elliptical arc-shaped, irregularly-shaped, etc.) profile, which may lead to the tissue engagement tip 320. In one or more embodiments in which the hook portion 318 includes a circular curved portion, the curved profile of the hook portion 318 may be defined by a radius of curvature R1 and an arc length AL1, each of which can influence the physical properties of the hook portion 318. For example, the radius of curvature R1 and the arc length AL1, among other things, can influence magnitude of recapture force required for removing a fixation anchor 302 from within the LAA 118. Removing the fixation anchor 302 from within the LAA 118 may be useful if the medical device 100 is placed at an undesired location in a patient's heart, and removal and/or adjustment is desired in order to place the medical device 100 at a different/desired location (e.g., where the medical device may seal off the LAA). Therefore, because the fixation anchors of the present disclosure may be fabricated separate and apart from the medical device body, dimensions of the fixation anchor or portions thereof (e.g., the fixation anchor height H1, the fixation anchor angle A1, etc.) may be selected to modify (e.g., reduce), for example, an amount of force for recapture or redeployment of the fixation anchor 302. For some medical procedures, reduced recapture force may be useful for reducing or avoiding tissue injury.

In at least one embodiment, the anchor body 314 can include an obstructive element 322 at or near the second end 306 of the anchor body 314 (as illustrated in FIG. 3C). The obstructive element 322 can have a width W7, which may be greater than one or more (e.g., all) of the respective widths W3, W4, and W5 of the second end 306, central portion 316, and first end 304 of the anchor body 314. In one or more embodiments, the obstructive element 322 and the hook portion 318 can be disposed opposite to each other (e.g., disposed on opposing ends of the anchor body 314, disposed on opposing sides of support structure 212, etc.). In at least one embodiment, the obstructive element 322 can be fabricated to have the width W7 which is greater than the width W2 of the one or more apertures 308. This may reduce (e.g., prevent) migration of the obstructive element 322 in the distal direction, which may reduce or prevent migration of the fixation anchor 302 within the support structure 212 and/or unintentional disengagement from the support structure 212 in response to a force applied in the distal direction. For example, when a medical device 100 of the present disclosure is implanted in the LAA 118, the obstructive element may counter a force distally applied by the LAA tissues on the hook portion of the fixation anchor.

In FIG. 3D, a fixation anchor 302 engages a support structure 212 by extending through the apertures 308a, 308b, and 308c. For example, as illustrated in FIG. 3D, the anchor body 314 and the support structure 212 can be engaged via interlocking, such as by interweaving the anchor body 314 and the support structure 212. In accordance with the illustrated embodiment of FIG. 3D, the fixation anchor 302 can be interweaved into the support structure 212 by successively feeding the fixation anchor through apertures 308a, 308b, and 308c, with the hook portion 318 protruding out of the aperture 308c of the support structure 212. In the illustrated embodiment, the support structure 212 includes more than one aperture 308 (e.g., 308a, 308b, 308c) and the fixation anchor 302 is configured to pass through the apertures (e.g., slots, holes, channels, passages, etc.), such as the apertures 308a, 308b, and 308c of the support structure 212, to form a weaving pattern. The fixation anchor 302 and the support structure 212 overlap in layers and cross each other to prevent unintentional migration of the fixation anchor 302 from the support structure 212. It may be recognized that the fixation anchor 302 depicted in FIGS. 3C and 3D may be removed from the support structure 212 by applying a proximal force on the fixation anchor and reversing the interweaving used to engage the fixation anchor 302 with the support structure 212.

As mentioned above, the fixation anchor 302 can be fabricated separate and apart from the medical device body 206. In at least one embodiment, the anchor body 314 of the fixation anchor 302 can be configured to engage with the medical device body 206 so as to be removably coupled to the support structure 212. In some embodiments, the anchor body 314 may engage a support structure 212 by forming a weld. In some embodiments, the anchor body 314 may engage the support structure 212 via an adhesive. In some embodiments, the anchor body 314 may engage the support structure 212 via a bond formation. In some embodiments, the anchor body 314 may engage the support structure 212 via a frictional fit. In some embodiments, the anchor body 314 may engage the support structure 212 via a combination of the aforementioned techniques or any other techniques known in the art.

The separate fabrication of the fixation anchor 302 from the medical device body 206 may allow additional design flexibility in terms of material selection and dimensional selection before fabrication. For example, at least some manufacturing dimensions of the fixation anchor 302 may be selected more flexibly, relative to a medical device body design including an integral fixation anchor. For example, the thickness of the fixation anchor 302 need not be the same as the thickness of the medical device body. Further, the one or more materials of construction of the fixation anchor need not be the same as the one or more materials of construction of the medical device body. The widths W3, W4 and W5, in addition to the radius of curvature R1, the arc length AL1 and the thickness T1 of the hook portion 318, can be selected for attaining useful or suitable performance characteristics (e.g., fixation strength, flexural strength, stiffness, etc.) of the fixation anchor 302. In at least one embodiment, the hook portion 318 can be configured to protrude toward the tissues of the LAA 118 when the medical device 100 is implanted in the LAA 118.

Figure 3E:
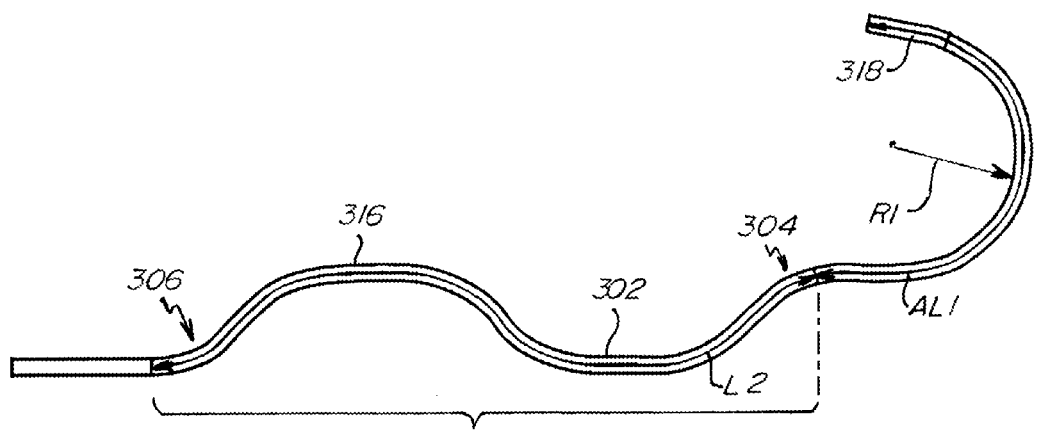
FIG. 3E is a side view of a fixation anchor, in accordance with at least one embodiment of the present disclosure.

FIG. 3E is a side view of the fixation anchor 302, in accordance with at least one embodiment of the present disclosure. In some embodiments, the central portion 316 can be formed of a shape memory alloy, which may facilitate disposing the central portion 316 at least partly into the aperture 308. In some embodiments, the central portion 316 can be formed of one or more other materials. FIG. 3E illustrates the fixation anchor 302 including an undulating structure. In one or more embodiments, an undulating structure may include alternating convex and concave curvatures and/or may include a plurality of inflection points along the undulating structure. In one or more embodiments, the central portion 314 of a fixation anchor 302 may include at least one undulating structure constructed and arranged to extend through at least two apertures (e.g., 2, 3, 4, 5, more than 5, etc.) defined by the first support structure.

Figure 3F:
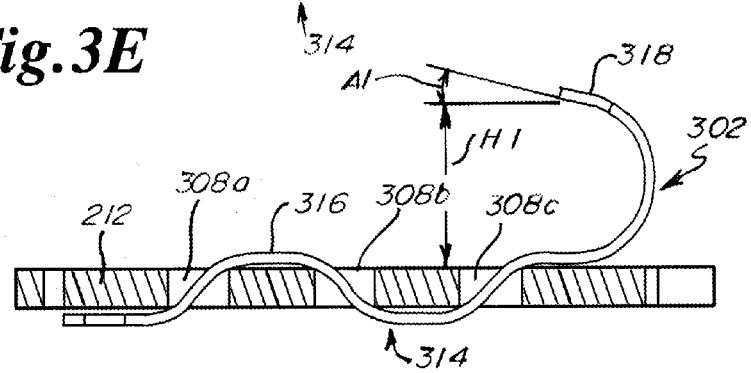
FIG. 3F is a side view of a fixation anchor disposed into a cross-section of a support structure, in accordance with at least one embodiment of the present disclosure.

For example, FIG. 3F is a side view of a fixation anchor 302 engaging a support structure 212, wherein the central portion 316 of the first anchor body 314 includes at least one undulating structure constructed and arranged to extend through at least two apertures (e.g., 308a, 308b, 308c) defined by the first support structure. In one or more embodiments, the undulating structure may facilitate engaging the fixation anchor 302 with the first support member 212 and/or may facilitate a reduction of unintentional fixation anchor migration by, for example, a distally applied force.

In at least one embodiment, the fixation anchor 302 can be configured to, for example, facilitate fixation of the medical device 100 within the LAA 118. The hook portion 318 can be configured to, for example, be removably coupled to tissues of the LAA 118 so as to provide support to the medical device 100. The medical device 100 can be configured so as to, for example, be recaptured and redeployed at the same or a different (e.g., desired) location. In one or more embodiments, the recapture force to recapture the fixation anchor 302 can be reduced by, for example, selecting a reduced thickness T1 of the hook portion 318 of the fixation anchor 302. For example, thickness T1 can be selected, independently of the thickness of a support structure, to influence migratory ability of the medical device 100 within the LAA 118, relative to other fixation anchor thickness selections. Separate fabrication of the fixation anchor 302 may allow the thickness T1 to be selected to, for example, impart a useful reduced (e.g., eliminated) migratory ability to the medical device 100 and/or to reduce the recapture force to recapture and redeploy the medical device 100.

In one or more embodiments, the separate fabrication of the medical device body 206 from the fixation anchor 302 can simplify the process of manufacturing the medical device 100. For example, the manufacturing process of the fins/barbs (e.g., a tissue engagement tip) of a fixation anchor may require high precision forming tools thereby increasing cost of production. The level of precision of tools to manufacture a medical device body may be comparatively less than that to fabricate a fixation anchor. Therefore, if a fixation anchor is manufactured as integral with a medical device body, relatively high precision tools may be required in the manufacturing of the medical device body. In contrast, the cost of production may be reduced by separately fabricating a fixation anchor with the use of relatively low precision tools. One of skill in the art will recognize that one or more other manufacturing advantages (e.g., reduced material waste, improved quality control, etc.) may be realized in one or more embodiments of the medical devices of the present disclosure. In addition, in one or more embodiments of the medical devices of the present disclosure, the interchangeability of fixation anchors may offer a wider range of medical treatment options for a given medical device body, which may accommodate a wider variety of patient physiologies (e.g., sizes, sensitivities, etc.). For example, the number of fixation anchors and/or the distance between fixation anchors may be selected. In one or more embodiments of the medical devices that include multiple fixation anchors, the shape and configuration of the fixation anchors may be mixed and/or matched to accomplish one or more treatment objectives.

Figure 4:
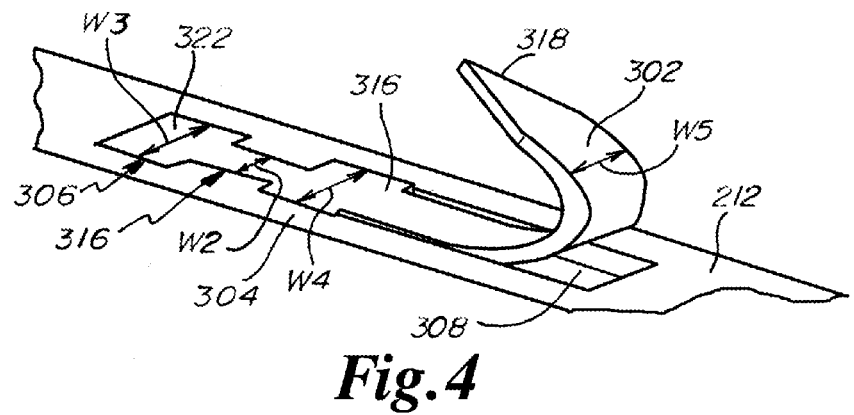
FIG. 4 is a perspective view of a fixation anchor coupled to a support structure of a medical device, in accordance with at least one embodiment of the present disclosure.

With reference to FIG. 4, in some embodiments, an aperture 308 may be formed as a depression (e.g., recess, indentation, etc.) into a body wall 214 of a support structure 212. As shown in FIG. 4, in one or more embodiments, an obstructive element 322 can be disposed within at least a portion of the aperture 308. For example, the obstructive element 322 of FIG. 4 is received by a portion of an aperture 308 and may remain fixed within the aperture 308 (e.g., to facilitate coupling of the fixation anchor 302 with the support structure 212). As shown in FIG. 4, the widths W3, W4, and W5 of the second end 306, the central portion 316, and the first end 304 are less than or equal to (e.g., no greater than) a width W2 of the aperture 308, which can be adapted to receive at least a portion of the anchor body 314. As shown, the shape of a portion of the depression (e.g., aperture 308) conforms to the shape of at least a portion of the obstruction element 322 and the central portion 316 of the first anchor body 314. In one or more embodiments, shape conformation may facilitate fixation and may reduce the ability of the fixation anchor 302 to migrate distally (e.g., in response to a distally applied force). In at least one embodiment, the obstructive element 322 and the central portion 316 may be disposed into the aperture 308 via any suitable engagements known to one of skill in the art (e.g., a weld, an adhesive such as a UV-curable adhesive, a bond, a friction fit, an interweave, an interlock, combinations thereof, etc.). It may be recognized that the thickness of the fixation anchor 302, or any portion thereof (e.g., obstruction element 322, hook portion 318, etc.) may or may not be the same as the thickness of the support structure 212 and may or may not be the same depth as the aperture 308. In one or more embodiments, at least a portion of the fixation anchor 302 may be flush with at least one side of support structure 212. Another aspect of the present disclosure relates to a method of making a medical device (e.g., medical device 100). The method includes providing a medical device body (e.g., medical device body 206) that includes a first support structure (e.g., first support structure 212), as described herein. The method also includes providing a first fixation anchor (e.g., first fixation anchor 302) formed separate and apart from the medical device body, as described herein, and attaching the first fixation anchor to the first support structure, wherein the first fixation anchor is structured and arranged to be detached from the first support structure and reattached to the first support structure or to a second support structure of the first medical device body or to a second medical device body.

A method of making a medical device may be performed to make, for example, any of the medical devices disclosed herein including, but not limited to an implantable medical device, an occlusion device, a left atrial appendage occlusion device, and/or an interior vena cava filter.

In one or more embodiments of the present disclosure, the support structure 212 can be made of a medical grade material. For example, in some embodiments, the support structure 212 can be made of nitinol or any other expendable spring loaded or balloon expandable material. In at least one embodiment of the presently disclosed methods, the fixation anchor 302 can be formed separate and apart from a medical device body 206 of the medical device 100 by using, for example, any of the techniques described above. In some embodiments, the fixation anchor 302 can be formed from a first material that is the same as a second material of the support structure 212. In some embodiments, the fixation anchor 302 can be formed of a first material different that is different from a second material of the support structure 212. Any of a wide variety of materials may be suitable for the fixation anchor and the support structure. For example, suitable materials may include, but are not limited to, stainless steel, nitinol, nylon, polyester, polyethylene, polyethylene terephthalate (PET), and combinations thereof.

In the present disclosure, a fixation anchor 302 may engage with the support structure 212 in any of a wide variety of manners known to one of skill in the art including, but not limited to, a weld, an adhesive, a bond, a friction fitting, an interweaving, an interlocking, and combinations thereof.

A description of some embodiments of the present disclosure is contained in the following numbered statements:

1. A medical device comprising:
   a medical device body comprising a first support structure; and
   a first fixation anchor comprising:

a first anchor body extending between a first end and an opposing second end; and
a hook portion extending from the first end,
wherein the first anchor body engages the first support structure,
wherein the first fixation anchor is fabricated separate and apart from the medical device body; and wherein the first fixation anchor is formed from a first material and the medical device body is formed from a second material that is the same as or different from the first material.

2. The medical device of statement 1 wherein the first anchor body is constructed and arranged to be removable from the first support structure.

3. The medical device of any of statements 1 and 2 further comprising a second fixation anchor that is interchangeable with the first fixation anchor.

4. The medical device of any of statements 1-3 wherein the medical device body further comprises a second support structure and wherein the first fixation anchor is interchangeable between the first support structure and the second support structure.

5. The medical device of any of statements 1-4 wherein the first anchor body and the first support structure are engaged via an engagement selected from the group consisting of a weld, an adhesive, a bond, a friction fit, an interweave, an interlock, and combinations thereof.

6. The medical device of any of statements 1-5 wherein the first support structure defines an aperture extending through a wall of the medical device body, wherein at least a portion of the first anchor body is disposed within at least a portion of the aperture.

7. The medical device of any of statements 1-6 wherein the first anchor body further comprises an obstructive element at or near the second end of the first anchor body and a central portion disposed between the obstructive element and the first end, wherein the obstructive element has a width greater than a width of the central portion.

8. The medical device of statement 7 wherein the width of the central portion is constant between the obstruction element and the first end and is no greater than the width of the portion of the aperture in which the portion of the first anchor body is disposed.

9. The medical device of any of statements 7 and 8 wherein the central portion comprises at least one undulating structure constructed and arranged to extend through at least two apertures defined by the first support structure.

10. The medical device of any of statements 7-9 wherein the obstruction element and the hook portion are disposed on opposite sides of the wall of the medical device body.

11. The medical device of any of statements 7-10 wherein the obstruction element is disposed within a portion of the aperture.

12. The medical device of any of statements 7-11 wherein the central portion of the first anchor body is disposed within a portion of the aperture.

13. The medical device of any of statements 7-12 wherein the shape of the aperture coincides with the shape of the obstruction element and central portion of the first anchor body.

14. The medical device of any of statements 1-13 wherein the medical device is an implantable medical device, an occlusion device, a left atrial appendage occlusion device, or an interior vena cava filter.

15. The medical device of any of statements 1-14 further comprising a covering surrounding at least a portion of the medical device body.

16. The medical device of statement 15, wherein the covering includes a plurality of pores configured for blood clot filtration.

17. The medical device of any of statements 15 and 16, wherein the covering is formed from a biocompatible material.

18. A method of making a medical device comprising:
providing a medical device body comprising a first support structure;
providing a first fixation anchor formed separate and apart from the medical device body; and
attaching the first fixation anchor to the first support structure;
wherein the first fixation anchor is structured and arranged to be detached from the first support structure and reattached to the first support structure or to a second support structure of the first medical device body or to a second medical device body.

19. The method of statement 18, wherein attaching comprises performing at least one of a welding, an adhesive fixation, a bonding, a friction fitting, an interweaving, an interlocking, and combinations thereof.

The above disclosure is intended to be illustrative and not exhaustive. This description will suggest many variations and alternatives to a person of ordinary skill in this art. The various elements shown in the individual figures and described above can be combined or modified for combination as desired. All these alternatives and variations are intended to be included within the scope of the claims where the term "comprising" means "including, but not limited to".

Further, the particular features presented in the dependent claims can be combined with each other in other manners within the scope of the present disclosure such that the present disclosure should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g., each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

Those skilled in the art can recognize other equivalents to the specific embodiments described herein which equivalents are intended to be encompassed by the claims attached hereto.

The invention claimed is:

1. A medical device comprising:
a medical device body comprising a unitary frame wall having proximal portion, a distal portion and a plurality of first support structures therebetween; and
a plurality of first fixation anchors each comprising:
a first anchor body extending between a first end and an opposing second end; and
a hook portion extending from the first end,
wherein each first anchor body engages an associated first support structure of the plurality of first support structures in a fixed longitudinal relationship in a first configuration, wherein the first fixation anchor is fabricated separate and apart from the associated first support structure of the plurality of first support structures; and wherein each first fixation anchor is formed from a first material and each first support structure of the plurality of first support structures is formed from a second material that is the same as or different from the first material, wherein the plurality of first support structures each define an aperture extending through a wall of the medical device body, wherein at least a portion of a first anchor body is disposed within at least a portion of the aperture, wherein each first anchor body further comprises an obstruction element at or near the second end of the first anchor body and a central portion disposed between the obstructive element and the first end, wherein the obstructive element has a width greater than a width of the central portion.

2. The medical device of claim 1 wherein each first anchor body is constructed and arranged to be removable from the first support structure in a second configuration.

3. The medical device of claim 1 further comprising a second plurality of fixation anchors that is interchangeable with the first plurality of fixation anchors.

4. The medical device of claim 1 wherein the medical device body further comprises a second plurality of support structures and wherein a first fixation anchor is interchangeable between the first support structure and the second support structure.

5. The medical device of claim 1 wherein the first anchor body and the first support structure are engaged via an engagement selected from the group consisting of a weld, an adhesive, a bond, a friction fit, an interweave, an interlock, and combinations thereof.

6. The medical device of claim 1 wherein the width of the central portion is constant between the obstruction element and the first end and is no greater than the width of the portion of the aperture in which the portion of the first anchor body is disposed.

7. The medical device of claim 6 wherein the central portion comprises at least one undulating structure constructed and arranged to extend through at least two apertures defined by the first support structure.

8. The medical device of claim 7 wherein the obstruction element and the hook portion are disposed on opposite sides of the wall of the medical device body.

9. The medical device of claim 1 wherein the obstruction element is disposed within a portion of the aperture.

10. The medical device of claim 9 wherein the central portion of the first anchor body is disposed within a portion of the aperture.

11. The medical device of claim 10 wherein the shape of the aperture coincides with the shape of the obstruction element and central portion of the first anchor body.

12. The medical device of claim 1 wherein the medical device is an implantable medical device, an occlusion device, a left atrial appendage occlusion device, or an interior vena cava filter.

13. The medical device of claim 1 and further comprising a covering surrounding at least a portion of the medical device body.

14. The medical device of claim 13, wherein the covering includes a plurality of pores configured for blood clot filtration.

15. The medical device of claim 13, wherein the covering is formed from a biocompatible material.

* * * * *